United States Patent
Sackner et al.

(10) Patent No.: US 6,783,498 B2
(45) Date of Patent: Aug. 31, 2004

(54) METHOD AND SYSTEM FOR EXTRACTING CARDIAC PARAMETERS FROM PLETHYSMOGRAPHIC SIGNALS

(75) Inventors: Marvin A. Sackner, Miami, FL (US); Dana Michael Inman, Miami, FL (US)

(73) Assignee: Vivometrics, Inc., Ventura, CA (US)

( * ) Notice: Subject to any disclaimer, the term of this patent is extended or adjusted under 35 U.S.C. 154(b) by 231 days.

(21) Appl. No.: 10/107,078

(22) Filed: Mar. 27, 2002

(65) Prior Publication Data

US 2003/0187341 A1 Oct. 2, 2003

(51) Int. Cl.$^7$ .................................................. A61B 5/02
(52) U.S. Cl. ...................... 600/481; 600/509; 600/521; 600/508; 600/506
(58) Field of Search .................................. 600/481, 483, 600/504, 506, 507, 508, 509, 513, 519, 521, 485, 301, 300, 500; 128/925, 923, 920

(56) References Cited

U.S. PATENT DOCUMENTS

| RE35,122 E | 12/1995 | Corenman et al. |
| 5,533,511 A | 7/1996 | Kaspari et al. |
| 5,584,295 A | * 12/1996 | Muller et al. ............ 600/300 |
| 6,067,462 A | 5/2000 | Diab et al. |

* cited by examiner

Primary Examiner—Mary Beth Jones
Assistant Examiner—Navin Natnithithadha
(74) Attorney, Agent, or Firm—Ohlandt, Greeley, Ruggiero & Perle

(57) ABSTRACT

A method and system for extracting cardiac parameters from a plethysmographic signal is described wherein the plethysmographic signal is passed through a first filter to remove non-cardiac components of the signal. A second filter averages a plurality of cardiac cycles and cardiac parameters are extracted from the averaged cardiac signal.

30 Claims, 3 Drawing Sheets

METHOD AND SYSTEM FOR EXTRACTING CARDIAC PARAMETERS FROM PLETHYSMOGRAPHIC SIGNALS

FIELD OF THE INVENTION

The present invention relates to the field of ambulatory and non-invasive monitoring of an individual's physiological parameters. In particular, the invention relates to an apparatus and method for extracting a cardiac signal from a signal generated by a thoracocardiograph (TCG) that may also contain respiratory and motion/noise signals.

BACKGROUND OF THE INVENTION

As used herein, "plethysmography", and its derivative words, is the measurement of a cross-sectional area of a body. "Inductive plethysmography" is a plethysmographic measurement based on determination of an inductance or a mutual inductance. A "plethysmographic signal" is a signal generated by plethysmography, and specifically by inductive plethysmography. The cross-sectional area of the body measured by a plethysmograph, also referred to herein as a thoracocardiograph (TCG), may include, singly or in combination, the chest, abdomen, neck, or arm.

The inductance sensor may be as simple as a conductive loop wrapped around the body cross-section. The loop is attached to a close-fitting garment that expands and contracts with the body cross-section. As the body cross-section expands and contracts, the area enclosed by the loop also expands and contracts thereby changing the inductance of the loop. The inductance change of the loop may be converted to an electrical signal using methods known to one of skill in the electrical art.

If the loop is placed around the chest, the changes in the loop inductance may be correlated to respiration volumes. For example, U.S. Pat. No. 4,308,872 ("'872 patent"), issued Jan. 5, 1982 and titled "Method and Apparatus for Monitoring Respiration," discloses a method and apparatus for monitoring respiration volumes by measuring variations in the patient's chest cross sectional area and is herein incorporated by reference in its entirety.

In addition to measuring respiration volumes, a plethysmograph may also measure cardiac volumes and aortic pulses as described in U.S. Pat. No. 5,178,151 ("'151 patent"), issued Jan. 12, 1993 and titled "System for Non-invasive Detection of Changes of Cardiac Volumes and Aortic Pulses," and herein incorporated by reference in its entirety.

U.S. Pat. No. 6,047,203 ("'203 patent"), issued Apr. 4, 2000 and titled "Physiologic Signs Feedback System," discloses a non-invasive physiologic signs monitoring device which includes a garment that may be worn and has a plurality of sensors disposed on the garment such that respiratory and cardiac signs may be measured and transmitted to a remote device. The '203 patent is herein incorporated by reference in its entirety.

Co-pending U.S. patent application Ser. No. 09/836,384 ("'384 application"), filed on Apr. 17, 2001 and titled "Systems and Methods for Ambulatory Monitoring of Physiological Parameters," discloses a system and method for non-invasive, ambulatory monitoring of pulmonary and cardiac parameters and is herein incorporated by reference in its entirety.

The plethysmographic, or TCG, signal generated by the inductance sensor placed around the chest will be composed of essentially three signals generated from different sources. The first, and largest component of the TCG signal is caused by respiration and has a characteristic frequency that varies from about 12 breaths per minute to about 30 breaths per minute. The second, and smaller, component of the TCG signal is generated by the expansion and contraction of the heart within the chest cavity and is characterized by a frequency that varies from about 50 beats per minute to about 100 beats per minute (or more) in the resting state. The third component of the TCG signal is caused by motion or noise and cannot be characterized by a narrow range of frequencies. In order to extract cardiac parameters from the TCG signal, the cardiac component must be separated from the respiratory and noise components of the TCG signal. Although no further mention of the noise component of the TCG signal will be made, when referring to the respiratory, or pulmonary, component of the TCG signal, it should be understood to include the noise or motion component of the TCG signal as well.

Separating the cardiac signal from the pulmonary signal in the plethysmograph signal is difficult, if not impossible, for two reasons. First, the cardiac and pulmonary signals are composite signals having component frequencies close to each other (for example, 0.8–1.7 Hz cardiac frequency, 0.2–0.5 Hz pulmonary frequency) making frequency separation of the signals difficult. Moreover, the harmonics of the component frequencies of the respiratory signal lie directly within the spectrum defining the cardiac signal thereby making the complete separation of the cardiac signal from the respiratory signal impossible. Complete separation of the cardiac and respiratory signals, however, is not required for cardiac parameter extraction but will affect the resolution and accuracy of the extracted cardiac parameter. Furthermore, the frequencies of both the cardiac and pulmonary signals may change at different rates depending on the physical exertion of the subject. Second, the relative amplitude of the cardiac signal may be approximately 20 times smaller than the pulmonary signal and can vary by as much as a factor of three depending on the level of physical exertion thereby requiring very efficient removal of the pulmonary signal in order to recover the cardiac signal.

Two methods for separating the cardiac signal from the pulmonary signal are disclosed in the '151 patent. The first method takes cardiac measurements only during breath-holding thereby eliminating the pulmonary contribution to the plethysmograph signal. Breath-holding is intrusive, however, and may cause discomfort to the subject. The second method averages the plethysmograph signal based on an external trigger signal associated with a cardiac event such as the R wave of an EKG or the upstroke of a systemic arterial pulse. The disadvantage of the average method is the loss of fine details due to the averaging.

Therefore, there remains a need for more efficient signal processing of the plethysmograph signal and extraction of the cardiac signal.

Citation or identification of any references in this Section or any section of this Application shall not be construed that such reference is available as prior art to the present invention.

SUMMARY OF THE INVENTION

One aspect of the present invention is directed to a method for extracting cardiac parameters from a plethysmographic signal, the plethysmographic signal being responsive to at least one cardiac parameter, the method comprising the steps of: performing a frequency domain filtering operation on the plethysmographic signal producing a first filtered signal; performing a time domain filtering operation on the first filtered signal, producing a second filtered signal; and extracting the cardiac parameter from the second filtered signal. The frequency domain filtering operation may include a band-pass filter and furthermore be characterized by a lower corner frequency that is determined by a heart rate.

Another aspect of the present invention is directed to a method for extracting cardiac parameters from a plethysmographic signal, the plethysmographic signal being responsive to at least one cardiac parameter, the method comprising the steps of: performing a frequency domain filtering operation on the plethysmographic signal producing a first filtered signal; performing a time domain filtering operation on the first filtered signal, producing a second filtered signal; and extracting the cardiac parameter from the second filtered signal wherein the time domain filtering operation that includes an ensemble averaging operation.

The ensemble averaging operation further comprises the steps of: associating a plurality of segments of the plethysmographic signal with events characteristic of a cardiac cycle; shifting a plurality of segments to align the events associated with each of the plurality of events characteristic of the cardiac cycle; constructing an ensemble averaged cardiac cycle signal from the average of the plurality of aligned segments. The event characteristic of a cardiac cycle comprises an indicia derived from the electrocardiographic R-wave. The ensemble averaging operation further includes the step of reconstructing a thoracocardiograph signal from the ensemble averaged cardiac cycle signal.

Another aspect of the present invention is directed to a method for extracting cardiac parameters from a plethysmographic signal, the plethysmographic signal being responsive to at least one cardiac parameter wherein the cardiac parameter is a stroke volume.

Another aspect of the present invention is directed to a method for extracting cardiac parameters from a plethysmographic signal, the plethysmographic signal being responsive to at least one cardiac parameter wherein the cardiac parameter is a cardiac output.

Another aspect of the present invention is directed to a method for extracting cardiac parameters from a plethysmographic signal, the plethysmographic signal being responsive to at least one cardiac parameter wherein the cardiac parameter is a pre-ejection period.

Another aspect of the present invention is directed to a method for extracting cardiac parameters from a plethysmographic signal, the plethysmographic signal being responsive to at least one cardiac parameter wherein the cardiac parameter is a peak ejection rate.

Another aspect of the present invention is directed to a method for extracting cardiac parameters from a plethysmographic signal, the plethysmographic signal being responsive to at least one cardiac parameter wherein the cardiac parameter is the time to peak ejection rate.

Another aspect of the present invention is directed to a system for extracting cardiac parameters from a plethysmographic signal, the plethysmographic signal being responsive to at least one cardiac parameter, the system comprising: a first frequency-domain filter receiving the plethysmographic signal, having a dynamic lower cutoff frequency, and producing a first-filtered signal, a second time-domain filter receiving the first filtered signal and producing a second filtered plethysmographic signal; and a processor for extracting the cardiac parameter from the second filtered signal.

Another aspect of the present invention is directed to a system for generating a thoracocardiograph signal comprising: a first digitizer for converting a first signal generated by an inductive plethysmographic sensor to a digitized first signal; a first digital filter for transforming the digitized first signal into a first filtered signal, the first filter characterized by a frequency pass-band based on a heart rate; and a second digital filter for transforming the first filtered signal into a thoracocardiograph signal, the second filter characterized by averaging segments of the first filtered signal based on events characteristic of the cardiac cycles.

Another aspect of the present invention is directed to a computer-readable medium comprising instructions for controlling a computer to generate a thoracocardiograph signal from a plethysmographic signal responsive to cardiac activity by frequency domain filtering the plethysmographic signal producing a first filtered signal; and time domain filtering the first filtered signal producing thoracocardiograph signal.

Another aspect of the present invention is directed to a method for extracting cardiac parameters from a plethysmographic signal characterized by a heart rate, the method comprising the steps of: performing a first band-pass filtering operation on the plethysmographic signal producing a first filtered signal, the first filtering operation characterized by a lower corner frequency less than the heart rate; performing a second band-pass filtering operation on the plethysmographic signal producing a second filtered signal, the second filtering operation characterized by a lower corner frequency greater than the lower corner frequency of the first filtering operation; interpolating the first filtered signal and the second filtered signal based on the heart rate to produce a filtered plethysmographic signal; and extracting cardiac parameters from the filtered plethysmographic signal.

Another aspect of the present invention is directed to a system for extracting cardiac parameters from a plethysmographic signal comprising: means for receiving a heart rate; a first filter characterized by a first lower corner frequency, the first lower corner frequency not greater than the heart rate, the first filter capable of receiving the plethysmographic signal and generating a first filtered signal; a second filter characterized by a second lower corner frequency, the second lower corner frequency greater than the first lower corner frequency, the second filter capable of receiving the plethysmographic signal and generating a second filtered signal; and a processor for generating a filtered plethysmographic signal by interpolating the first filtered signal and the second filtered signal based on the heart rate and extracting a cardiac parameter from the filtered plethysmographic signal.

BRIEF DESCRIPTION OF THE FIGURES

The present invention may be understood more fully by reference to the following detailed description of the preferred embodiment of the present invention, illustrative examples of specific embodiments of the invention and the appended figures in which.

DETAILED DESCRIPTION OF THE PREFERRED EMBODIMENT

Figure 1C:
FIG. 1C is a photograph showing a portion of the plethysmographic sensor mounted on the vest.
Figure 1B:
FIG. 1B is a photograph of a TCG sensor-mounted vest being worn by a patient.
Figure 1A:
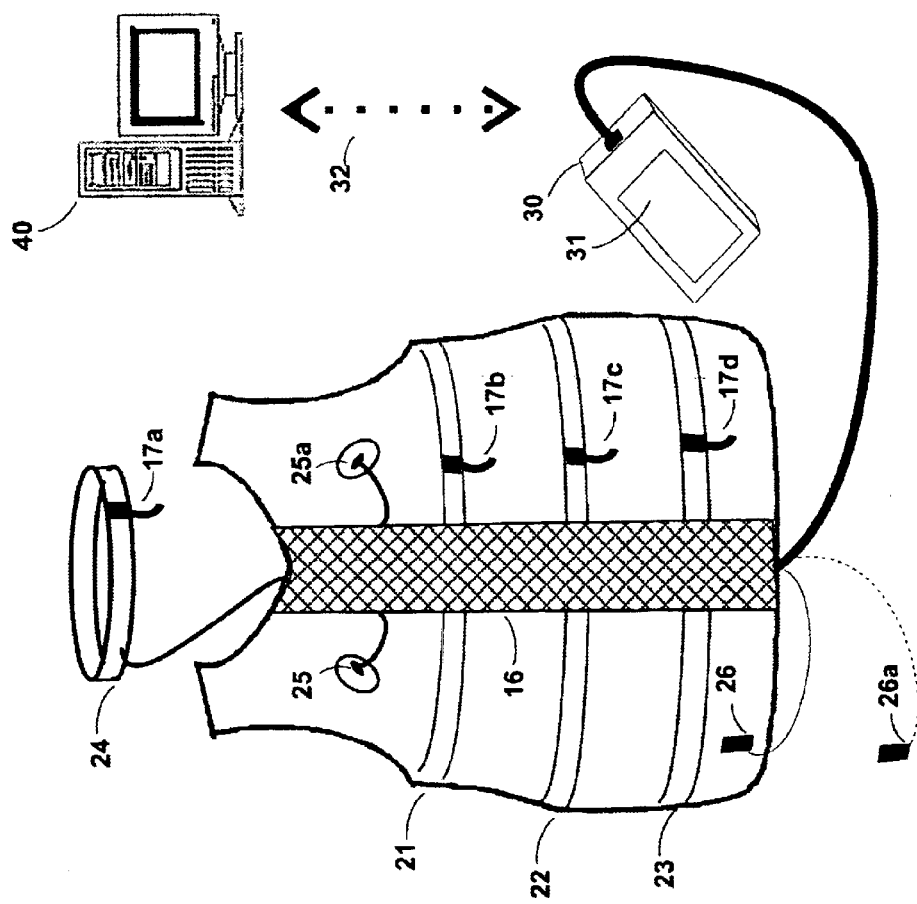
FIG. 1A is a diagrammatic representation showing the TCG sensors and their placement about a human torso.

FIGS. 1A–C are diagrammatic representations showing the TCG sensors and their placement about a human torso. The chest sensor 21 (FIGS. 1A and B) is preferably positioned just inferior to the axilla. The thoracic sensor 22 is preferably positioned just below the level of the xiphoid process. The abdominal sensor 20 is preferably positioned 1 to 2 cm superior to the umbilicus. The chest sensor 21 and abdominal sensor 20 are used to detect breathing patterns and are collectively referred to as a respiratory sensor. The position of the thoracic sensor 22 just below the xiphoid process enables the thoracic sensor 22 to detect the strongest cardiac plethysmographic signal relative to the other plethysmographic sensors and is used to generate the TCG. The respiratory sensor generates a respiratory plethysmographic signal that may be optional for generation of the TCG. Further sensors may be used in alternative embodiments.

Optional plethysmographic sensors may include a neck sensor 24 positioned around the neck, limb sensors (not illustrated) positioned around the wrist or elbow, and hemithoracic sensors (not illustrated) positioned around the left and right sides of the upper thorax.

In a preferred embodiment, each sensor is attached to, or embedded in, a garment 15 worn by the subject. The garment 15 is fitted using fastening devices 16 such as velco strips or zippers so that the garment and the sensors closely follow the expansion and contraction of the subject's body. Each sensor may be individually adjusted with individual tightening devices 17a–d. The plethysmographic sensors are preferably conductive coils encircling the appropriate portions of the body. Referring to FIG. 1C, each coil 18 is preferably disposed in a predetermined curvilinear pattern in an elastic band 19.

The coil, which may be a single loop of a conductor or may comprise a plurality of conductive loops, acts as an inductor in an electronic oscillator circuit known to one of skill in the art. Each coil is incorporated into a sensor electronic circuit that generates a signal having an oscillation frequency that varies in proportion to the expansion or contraction of the coil.

Referring again for FIG. 1A, the sensor electronics may be attached to, or embedded in, the garment 15 near each coil. Alternatively, the sensor electronics may be incorporated into a separate controller unit 30 that may be mounted directly to the garment 15 or may be carried by the subject. In addition to the sensor electronics, the controller 30 may contain additional electronics for data logging of the sensor signals, communication 32 with a remote computer 40, audio or visual communication with the subject, and signal processing of the sensor signals. In this embodiment, the controller may include a programmable device, such as a microprocessor or a digital signal processor, program and data memory, and interfaces all configured as is known in the art. Alternatively, signal processing of the sensor signals may be performed on the remote computer 40 and controller communication with the subject limited primarily to alarms in order to reduce the size and complexity of the controller unit 30 thereby making the monitoring process less intrusive on the subject. Communication 32 may be by wire, wireless or by computer readable media such as mini or micro drives, memory cards, and the like.

In a preferred embodiment, electrocardiograph (ECG) electrodes 25a and 25b are also in contact with the subject, by being, for example, mounted to the garment 15 and connected to the controller 30 or connected by means of wires to a data collection module (not shown) that also collects data from the inductance sensors, thereby enabling the measurement, processing, and/or recording of the subject's ECG.

Optionally, one or more accelerometers 26 and 26a may be in contact with the subject (also by being, for example, mounted to the garment 15) and connected to the controller 30 or to a data collection module (not shown). Alternatively, accelerometer, also referred to as a posture sensor, may be located on the ventral center-line on the abdomen band 23. Posture sensor 26a may be alternatively positioned on the thigh and function as a "sit vs. stand" sensor.

The controller 30 may process the signal from the accelerometers to determine the orientation of the subject and use the orientation information to modify the signal processing of the plethysmographic sensor signals, or simply present orientation information to the persons analyzing the data.

Figure 2:
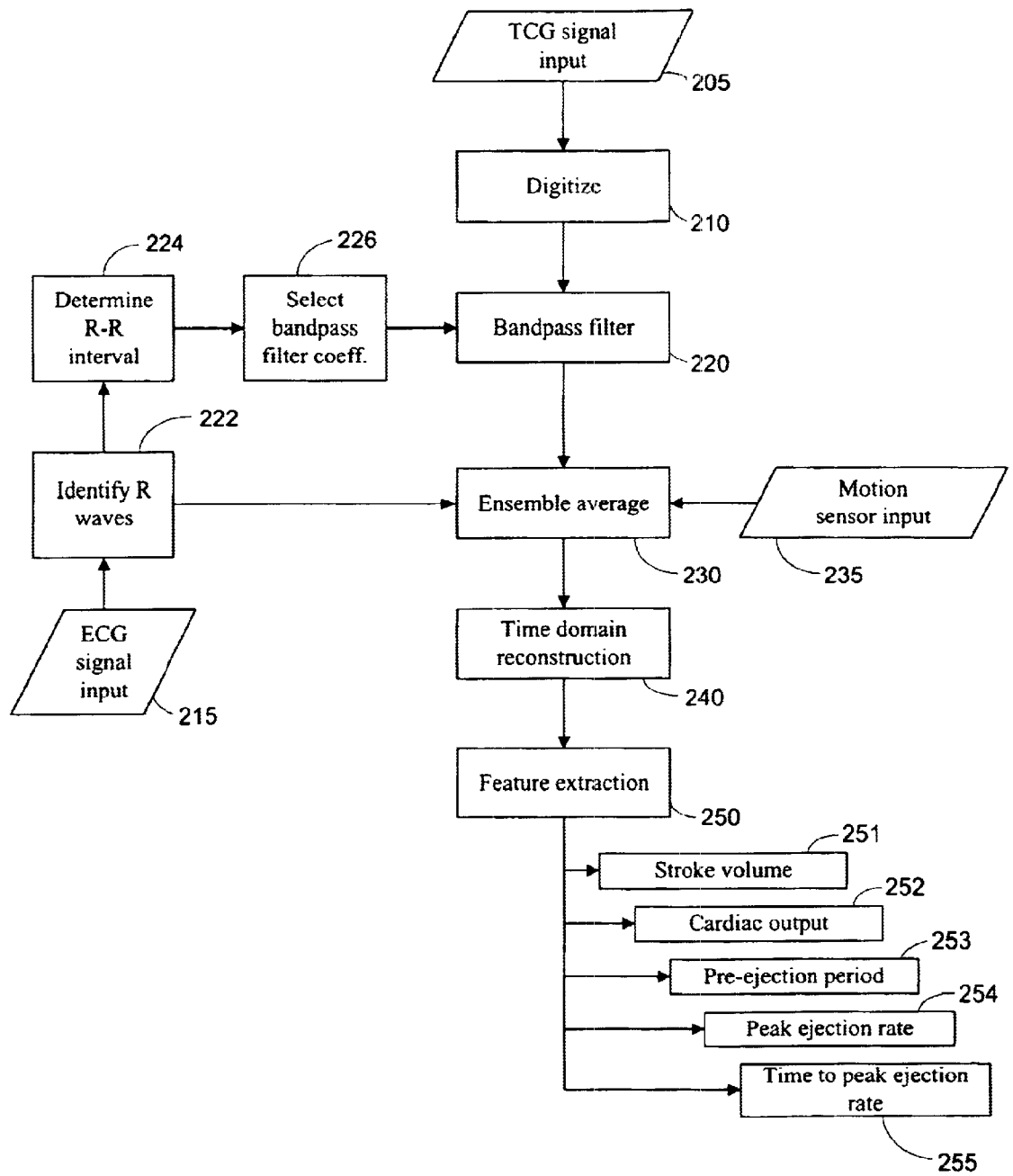
FIG. 2 is a block diagram of a preferred embodiment of the present invention.

FIG. 2 is a block diagram of the preferred embodiment of the present invention. The TCG signal 205 is directed into a digitizer 210 that samples the frequency of the TCG signal and generates a digital signal representing the cross-sectional area encircled by the plethysmographic sensor. In a preferred embodiment, the TCG signal is sampled at 200 Hz although any sampling rate substantially (1.3x) greater than the Nyquist sampling rate, which is twice the highest frequency of interest (about 10 Hz), is acceptable. The harmonics of the base frequency are important to the shape of the signal and carry the information needed for analysis. The selection of the sampling rate balances the desired level of detail in the signal against the signal processing hardware constraints and costs and is known to one of skill in the art.

In one embodiment, the TCG signal is quantized to a level such that the measured cross-sectional area is accurate to at least 10 ppm, more preferably to at least 5 ppm, and most preferably to 1 ppm.

The digitized TCG signal is directed to a band-pass filter 220 wherein the portion of the signal corresponding to the cardiac signal is passed through the frequency domain filter. The upper corner frequency is selected to minimize artifact signals arising from subject movement or noise. The inventors have discovered that increasing the upper corner frequency from 10 Hz to 30 Hz does not result in clinically apparent improvement in the signal. Therefore, in one embodiment of the present invention, the upper corner frequency of the band-pass filter may be selected in the range from 10–30 Hz. In a preferred embodiment, the upper corner frequency is about 10 Hz.

The lower corner frequency is dynamically adjusted according to the cardiac, or heart, rate (HR) determined, for example, from ECG electrodes 25 and 25a. Varying the lower corner frequency according to the heart rate allows the band-pass filter to separate the cardiac signal from the pulmonary signal over a range of physical exertions by the subject. The lower corner frequency is preferably above the frequency range of the pulmonary signal (usual between 0.2–0.5 Hz, which corresponds to a respiratory rate between 10 and 30 per minute) but sufficiently below the frequency range of the cardiac signal (usually between 0.7–2.0 Hz, which corresponds to a cardiac rate between 40 and 120 per minute) to allow the cardiac signal to pass through the filter without significant distortion from the filter roll-off. If the lower corner frequency is set too low, the cardiac signal will have a larger respiratory artifact signal but if the lower corner frequency is set too high, the attenuation of part of the TCG signal will distort the TCG waveform. A range from 0.6*HR to 0.8*HR for the lower corner frequency provides a reasonable balance between cardiac signal discrimination and cardiac signal distortion. In a preferred embodiment, the lower corner frequency is dynamically adjusted to 0.7*HR.

Figure 3A:
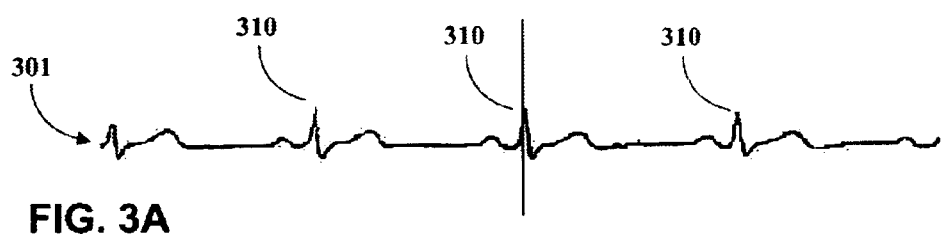
FIG. 3a shows a representative signal in time of an ECG.

In a preferred embodiment, the heart rate is determined from the ECG signal 215 generated by the ECG electrodes mounted on the subject. FIG. 3a shows an ECG signal that exhibits the sharply peaked and easily identified R-wave 310 signaling ventricular depolarization. The R-wave 310 is identified in 222 and the time interval between successive R-waves (the inverse of the heart rate) is calculated in 224. The R-wave is a large-amplitude, short-duration pulse relative to the remainder of the ECG signal and may be identified by a threshold filter or other such filter known to one of skill in the art. Other easily identified markers of ventricular systole may be used if available. In a preferred embodiment, the R-wave detector is implemented as an analog circuit that may be mounted on the garment 15. Several successive R—R intervals may be averaged to obtain a better estimate of the heart rate. In one embodiment, 15–50 R—R intervals are averaged to estimate the heart rate. In a preferred embodiment, a weighted average on a window comprising of 25 R—R intervals centered on the current heart beat is used to determine the heart rate. The weights may be set equal to 1/N where N is the number of heartbeats averaged. Alternatively, the weights may be adjusted to give more weight to the heartbeats closest to the current heartbeat and less weight to the more distant (from the current heartbeat) heartbeats.

The sampled heart rate signal is converted from discrete values to a continuous time signal and low pass filtered at a sampling rate of 25 Hz as is known to one of skill in the art. The smoothing of the heart rate signal by low pass filtering reduces the discontinuities in the heart rate and in the interpolated TCG signal.

The heart rate is used to select a set of filter coefficients corresponding to a band-pass filter having a lower corner frequency closest to the calculated heart rate in 226. In order to reduce the computational load on the processor, a plurality of band-pass filters having an upper corner frequency of 10 Hz and a range of lower corner frequencies covering the expected range of heart rates are designed using tools known to one of skill in the signal processing art. For example, one such design tool is the Matlab® computer program available from The MathWorks of Natick, Mass. The sets of filter coefficients defining each band-pass filter are stored in memory for quick access by the processor. As used herein, the term processor refers to any of a type of processor commonly used by one of skill in the signal processing art and may include DSPs, FGAs, and the like. In addition, the term processor as used herein also includes supporting circuitry and components such as memory, system bus, and I/O interfaces and the like.

In one embodiment, each point of the TCG signal is an interpolation of two filters having lower corner frequencies bracketing the sampled heart rate. For example, in one embodiment, ten filters are stored in memory having lower corner frequencies from 0.4 Hz through 2.2 Hz in increments of 0.2 Hz. If the desired lower corner frequency (0.7*HR) is below 0.4 Hz, the 0.4 Hz filter is used to filter the TCG signal. Similarly, if the desired lower corner frequency is above 2.2 Hz, the 2.2 Hz filter is used to filter the TCG signal. If the desired lower corner frequency is in the range from 0.4 Hz to 2.2 Hz, the filtered TCG signal is an interpolation of the two filters bracketing the desired lower corner frequency.

In another embodiment, an interpolated filter is created and used to filter the TCG signal. The interpolated filter is created by interpolating the filter coefficients from two of the pre-designed band-pass filters stored in the processor's memory that bracket the sampled heart rate. By way of example, if the sampled heart rate of 1.0 Hz, the preferred lower corner frequency of the band-pass filter should be 0.7 Hz. If the processor has stored the filter coefficients of band-pass filters having a lower corner frequency of 0.6 Hz and 0.8 Hz, the processor creates an interpolated filter having filter coefficients given by $$\hat{\omega}_i = (1-\alpha)\omega_i^{0.6} + \alpha\omega_i^{0.8} \qquad (1)$$

where $\hat{\omega}_i$ is the i-th coefficient for the interpolated filter, $\omega_i^{0.6}$ is the i-th coefficient of the pre-designed band-pass filter having a lower corner frequency below that of the desired lower corner frequency (in this example, the filter having a lower corner frequency of 0.6 Hz), $\omega_i^{0.8}$ is the i-th coefficient of the pre-designed band-pass filter having a lower corner frequency above that of the desired lower corner frequency (in this example, the filter having a lower corner frequency of 0.8 Hz), and $\alpha$ is the interpolation factor given by $$\alpha = \frac{0.7 * HR - lcf^-}{lcf^+ - lcf^-} \qquad (2)$$

where $lcf^-$ is the lower corner frequency of the pre-designed filter below the desired corner frequency and $lcf^+$ is the lower corner frequency of the pre-designed filter above the desired corner frequency.

The computational load on the processor may be further reduced by down-sampling the digitized TCG signal prior to the band-pass filter. In one embodiment, the digitized TCG signal is resampled from 200 Hz to 25 Hz by performing an 8-point running average. The TCG signal is up-sampled to 200 Hz after the band-pass filter by interpolation using a spline fit to the filtered signal.

Although band-pass filtering 220 removes most of the respiratory component from the TCG signal, the filtered signal still contains a respiratory artifact that affects the accuracy of the extracted cardiac features. In order to reduce the respiratory artifact to a level sufficient for accurate and automatic extraction of cardiac features during normal activities of daily living, a time domain filter is used to "smooth" the TCG signal. The band-pass filtered signal is directed to an averaging filter 230 that performs an ensemble average on the band-pass filtered signal.

The averaging filter 230 uses the R-wave signal 222 from the ECG electrode as a "clock" to indicate the same point in time relative to the cardiac cycle. The TCG component representing the cardiac signal will be correlated to the R-wave "clock" whereas the remaining components of the TCG signal, such as the respiratory component, will not be correlated to the R-wave "clock." The averaging filter 230 averages segments of the filtered TCG signal corresponding to a cardiac cycle, delimited by the R-wave "clock", by time shifting each cardiac cycle such that the R-wave for each cardiac cycle is aligned. The filter takes the average of several aligned cycles at each point along the cycle. Equation 3 describes the mathematical operation of the filter.

$$\hat{f}(n,t) = \sum_{i=-W}^{i=+W} w_i f(t + (R_{n+i} - R_n)) \quad (3)$$

In equation 3, f̂(n,t) is the ensemble averaged signal for the n-th cardiac cycle as a function of time, t, f(t) is the band-pass filtered TCG signal, $R_n$ is the time of the n-th cardiac cycle R-wave, $w_i$ are the cycle weights, and 2W+1 is the ensemble size.

The "beginning" and "end" of a cardiac cycle referenced to the R-wave "clock" may be determined to give clinically useful data. In a preferred embodiment, a cardiac cycle "begins" at approximately 20% of the R—R period before the R-wave and ends at approximately 80% of the R—R period after the R-wave. The cardiac component of the TCG signal will "reinforce" each other because they are correlated to the R-wave "clock." The respiratory component, however, will tend to cancel out because it is not correlated to the R-wave "clock".

The size of the ensemble or the number of cardiac cycles averaged should be large enough to allow the non-stationary (not correlated to the R-wave) components to average to zero or to an insignificant level, but small enough to remain responsive to changes in cardiac activity. The ensemble size may be between 20 beats and 500, preferably between 25 or 50 beats and 250 beats and most preferably approximately 100 or 150 beats (where W=75). The ensemble size may also be adjusted to higher or lower values depending on, for example, the physical exertion of the person. Preferably, if it is known that the non-stationary components have a greater presence in an TCG signal, then longer ensemble averages are advantageous to eliminate these artifacts, for example, 200, 250, and to 500 beat ensemble averages. If the contrary is known, then shorter ensemble averages are advantageous to preserve greater detail in the cardiac signal, for example, 100, 50, and down to 25 beat ensemble averages.

Optional motion sensors, such as accelerometers 26 and 26a in FIG. 1A, may be used, in optional step 235, to provide information about the extent of subject motion and current posture that can be used in this adjustment of W. The respiratory sensor may be used to provide information about the amplitude of respiration, such as subject breath holding, that may also be used for adjustment of W.

The cycle weights, $w_i$, may be set to 1/(2W+1) for a simple average. Preferably, $w_i$ may be adjusted to give more weight to the cardiac cycles closer to the current cardiac cycle and less weight to the cycles more distant (in time) from the current cardiac cycle. More preferably, $w_i$ may be adjusted by means of the previously described tools so that, when considered as defining a standard digital filter (the "equivalent" filter) operating on a signal sampled at a fixed time increment instead of relative to the R-wave clock, they define a low-pass equivalent filter with a narrow pass band and maximum stop band attenuation. Thereby, the cardiac signal, which is substantially constant (or has substantially zero frequency) at times fixed relative to the R-wave clock, may be filtered from the respiratory and other components, which are not constant with respect to times fixed relative to the R-wave (or have non-zero frequencies).

However, the pass band of the equivalent, low pass filter defined by $w_i$ should not be so narrow as to cause loss of clinically useful cardiac information. Most preferably, then, $w_i$ define an equivalent low pass filter, perhaps adjusted separately for each subject according to the subject's observed cardiac performance. Simply stated, the ensemble weights also serve to soften the onset of large "step" transition artifacts which pass the bandpass filter. As the step transition is rising slowly through the weights, other artifacts tend to cancel it before it achieves significant amplitude. Without the softening of the filter weights, the step would appear all at once, then be slowly "knocked back down" by canceling artifacts as they happen.

The TCG signal is reconstructed in step 240 by "stitching together" the ensemble averaged signal (where each output cardiac cycle is the ensemble average of (2*W+1) bandpass filtered, raw TCG signals). For example, the beginning of the n-th ensemble averaged cardiac cycle is stitched to the ending of the (n−1)-th ensemble average cardiac cycle and the ending of the n-th ensemble averaged cardiac cycle is stitched to the beginning of the (n+1)-th ensemble averaged cardiac cycle. Any discontinuities between successive cycles are smoothed by performing a linear interpolation between the two successive cycles over a transition region. In one embodiment, the transition region is between 10 and 30% of the cardiac period and in a preferred embodiment, the transition occurs over 20% of the cardiac period. Also, non-linear interpolation, such as spline interpolation and least square error fits may be used.

Figure 3B:
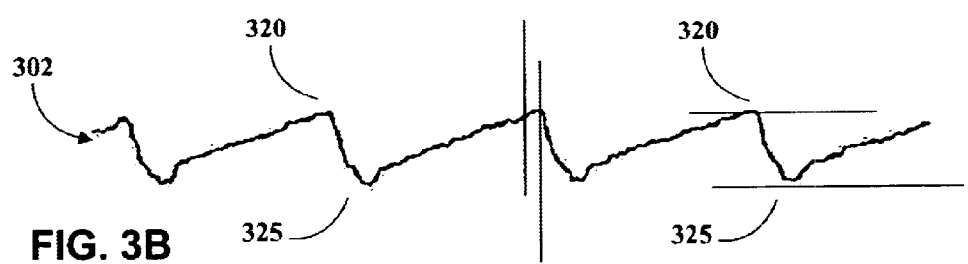
FIG. 3b shows a TCG signal after processing by a preferred embodiment of the present invention.
Figure 3C:
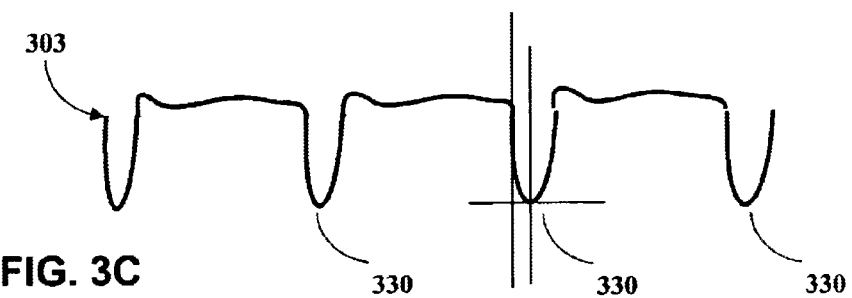
FIG. 3c shows the derivative of the TCG signal shown in FIG. 3b.

Once the time domain reconstruction is completed, cardiac feature extraction 250 is performed on the processed TCG signal. FIG. 3 shows the ECG 301, processed TCG 302, and the processed TCG derivative 303 signals aligned temporally and shows the cardiac features for each cardiac cycle extracted from the processed TCG signal. The derivative of the processed TCG signal 303 is generated from the processed TCG signal 302 using any of the common techniques for differentiating a signal known to one of skill in the art. The times of local maximums and minimums of the TCG signal 302 may be determined by locating the zero-crossing of the derivative signal 303 through the x-axis 335.

The stroke volume indicia (SV) 251 is the amplitude from the maximum 320 of the processed TCG sample to the next minimum 325 of the processed TCG signal 302. The cardiac output indicia (CO) 252 is the product of the stroke volume and the heart rate (CO=SV*HR). The peak ejection rate (PER) 254 is the minimum 330 of the processed TCG derivative signal 303. The SV and the CO so determined have been discovered by the inventors to be sufficiently accurate relative indicia of these cardiac parameters to be useful in clinical applications. Where a transformation has been measured relating the processed TCG signal to the actual cardiac volume, it may be used to obtain the actual SV and CO. Although measurement of such transformation currently requires such invasive techniques as thermal or dye dilution, such a measurement in a selected posture may serve to later normalize processed TCG signals obtained when the subject again assumes the selected posture.

The pre-ejection period (PEP) 253 is the time from the R-wave peak 310 to the maximum 320 of the processed TCG signal 302. The time to peak ejection rate (TPER) 255 is the time from the maximum 320 of the processed TCG signal 302 to the Peak Ejection Rate (PER) 330. Identification of the minimums and maximums of a signal is known to one of skill in the signal processing art and requires no further discussion.

After the minimums and maximums in signals 302 303 are identified, the cardiac parameters are determined by the processor and may be stored for later evaluation or displayed for evaluation. Other features of the cardiac volume signal may be extracted according to their known definitions.

The methods described herein may be programmed in any convenient computer language, such as assembly language, C, or C++, compiled into an executable form and stored on a computer readable medium for loading into the program memory of a programmable device. The present invention encompasses program products including such computer readable media. The present invention further encompasses systems, such as controller 30 or computer 40, configured by such executable software to carry out the described methods.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for extracting cardiac parameters from a plethysmographic signal, the plethysmographic signal being responsive to at least one cardiac parameter, the method comprising the steps of:
   (a) performing a frequency domain filtering operation on the plethysmographic signal producing a first filtered signal;
   (b) performing a time domain filtering operation on the first filtered signal, producing a second filtered signal; and
   (c) extracting the cardiac parameter from the second filtered signal.

2. The method of claim 1 wherein the frequency domain filtering operation includes a band-pass filter.

3. The method of claim 2 wherein the band-pass filter is characterized by a lower corner frequency that is determined by a heart rate.

4. The method of claim 1 wherein the time domain filtering operation is an ensemble averaging operation.

5. The method of claim 4 wherein the ensemble averaging operation further comprises the steps of:
   (i) associating a plurality of segments of the plethysmographic signal with events characteristic of a cardiac cycle;
   (ii) shifting a plurality of segments to align the events associated with each of the plurality of events characteristic of the cardiac cycle;
   (iii) constructing an ensemble averaged cardiac cycle signal from the average of the plurality of aligned segments.

6. The method of claim 5 where the event characteristic of a cardiac cycle comprises an indicia derived from the electrocardiographic R-wave.

7. The method of claim 5 wherein the ensemble averaging operation further includes the step of reconstructing a thoracocardiograph signal from the ensemble averaged cardiac cycle signal.

8. The method of claim 1 wherein the cardiac parameter is a stroke volume.

9. The method of claim 1 wherein the cardiac parameter is a cardiac output.

10. The method of claim 1 wherein the cardiac parameter is a pre-ejection period.

11. The method of claim 1 wherein the cardiac parameter is a peak ejection rate.

12. The method of claim 1 wherein the cardiac parameter is the time to peak ejection rate.

13. A system for extracting cardiac parameters from a plethysmographic signal, the plethysmographic signal being responsive to at least one cardiac parameter, the system comprising:
   (a) a first frequency-domain filter receiving the plethysmographic signal, having a dynamic lower cutoff frequency, and producing a first-filtered signal,
   (b) a second time-domain filter receiving the first filtered signal and producing a second filtered plethysmographic signal; and
   (c) a processor for extracting the cardiac parameter from the second filtered signal.

14. The system of claim 13 wherein the lower cutoff frequency is greater than a respiratory rate and less than a cardiac rate.

15. The system of claim 13 wherein the lower corner frequency is determined by a cardiac rate.

16. The system of claim 15 wherein the lower corner frequency is between 0.6*HR and 0.8*HR where HR is the cardiac rate.

17. The system of claim 15 wherein the lower corner frequency is approximately 0.7*HR where HR is the cardiac rate.

18. The system of claim 13 wherein the second filter is an ensemble averaging filter characterized by the equation $$\hat{f}(n, t) = \sum_{i=-W}^{i=+W} w_i f(t + (R_{n+i} - R_n))$$

where $\hat{f}(n,t)$ is an ensemble averaged signal for the n-th cardiac cycle as a function of time, t, f(t) is a filtered TCG signal, $R_n$ is the time of the n-th cardiac cycle R-wave, $w_i$ are the cycle weights, and 2W+1 is the ensemble size.

19. The system of claim 18 wherein the ensemble size is between 25 and 500.

20. The system of claim 18 wherein the ensemble size is between 50 and 250.

21. The system of claim 18 wherein the ensemble size is approximately 150.

22. A system for generating a thoracocardiograph signal comprising:
   (a) a first digitizer for converting a first signal generated by an inductive plethysmographic sensor to a digitized first signal;
   (b) a first digital filter for transforming the digitized first signal into a first filtered signal, the first filter characterized by a frequency pass-band based on a heart rate; and
   (c) a second digital filter for transforming the first filtered signal into a thoracocardiograph signal, the second filter characterized by averaging segments of the first filtered signal based on events characteristic of the cardiac cycles.

23. The thoracocardiograph of claim 22 further comprising a plethysmographic inductive sensor for generating the first signal.

24. The thoracocardiograph of claim 22 further comprising a electrocardiograph for determining the heart rate and for providing indicia of events characteristic of the cardiac cycles.

25. A computer-readable medium comprising instructions for controlling a computer to generate a thoracocardiograph signal from a plethysmographic signal responsive to cardiac activity by:

(a) frequency domain filtering the plethysmographic signal producing a first filtered signal; and
(b) time domain filtering the first filtered signal producing thoracocardiograph signal.

26. The computer-readable medium of claim 25 further comprising instructions for controlling the computer to extract at least one of the cardiac parameter from the thoracocardiograph signal.

27. The computer-readable medium of claim 25 further comprising instructions for controlling the computer to receive the plethysmographic signal from an inductive plethysmographic sensor.

28. A method for extracting cardiac parameters from a plethysmographic signal characterized by a heart rate, the method comprising the steps of:
(a) performing a first band-pass filtering operation on the plethysmographic signal producing a first filtered signal, the first filtering operation characterized by a lower corner frequency less than the heart rate;
(b) performing a second band-pass filtering operation on the plethysmographic signal producing a second filtered signal, the second filtering operation characterized by a lower corner frequency greater than the lower corner frequency of the first filtering operation;
(c) interpolating the first filtered signal and the second filtered signal based on the heart rate to produce a filtered plethysmographic signal; and
(d) extracting cardiac parameters from the filtered plethysmographic signal.

29. The method of claim 28 further including the step of averaging the filtered plethysmographic signal prior to extracting the cardiac parameters.

30. A system for extracting cardiac parameters from a plethysmographic signal comprising:
(a) means for receiving a heart rate;
(b) a first filter characterized by a first lower corner frequency, the first lower corner frequency not greater than the heart rate, the first filter capable of receiving the plethysmographic signal and generating a first filtered signal;
(c) a second filter characterized by a second lower corner frequency, the second lower corner frequency greater than the first lower corner frequency, the second filter capable of receiving the plethysmographic signal and generating a second filtered signal; and
(d) a processor for generating a filtered plethysmographic signal by interpolating the first filtered signal and the second filtered signal based on the heart rate and extracting a cardiac parameter from the filtered plethysmographic signal.

* * * * *